(12) United States Patent
Choubey et al.

(10) Patent No.: US 7,685,262 B2
(45) Date of Patent: Mar. 23, 2010

(54) METHOD AND SYSTEM FOR TRANSFER OF IMAGING PROTOCOLS AND PROCEDURES

(75) Inventors: Suresh K. Choubey, Delafield, WI (US); Tsur Bernstein, Glendale, WI (US); Sandeep N. Gupta, Glen Burnie, MD (US); Mohsin S. Dawoodbhai, Waukesha, WI (US); April Dorcas, Milwaukee, WI (US); Ashish M. Shah, Clifton Park, NY (US); Mani Sundararajan, Pewaukee, WI (US); John W. Zingsheim, Pewaukee, WI (US)

(73) Assignee: General Electric Company, Schenectady, NY (US)

( * ) Notice: Subject to any disclaimer, the term of this patent is extended or adjusted under 35 U.S.C. 154(b) by 1583 days.

(21) Appl. No.: 10/350,529

(22) Filed: Jan. 24, 2003

(65) Prior Publication Data

US 2004/0148403 A1 Jul. 29, 2004

(51) Int. Cl.
*G06F 15/177* (2006.01)

(52) U.S. Cl. .................. 709/220; 600/437; 705/2; 705/3; 709/221; 709/222

(58) Field of Classification Search ............ 705/2, 705/3; 600/437
See application file for complete search history.

(56) References Cited

U.S. PATENT DOCUMENTS

| | | | | |
|---|---|---|---|---|
| 5,715,823 A * | 2/1998 | Wood et al. | ........... | 600/437 |
| 5,831,612 A * | 11/1998 | Stoval et al. | ........... | 715/792 |
| 5,891,035 A * | 4/1999 | Wood et al. | ........... | 600/437 |
| 6,029,138 A * | 2/2000 | Khorasani et al. | ........... | 705/2 |
| 6,092,102 A * | 7/2000 | Wagner | ........... | 340/7.29 |
| 6,149,585 A * | 11/2000 | Gray | ........... | 600/300 |
| 6,196,970 B1 * | 3/2001 | Brown | ........... | 600/300 |
| 6,272,469 B1 * | 8/2001 | Koritzinsky et al. | ........... | 705/2 |
| 6,275,869 B1 * | 8/2001 | Sieffert et al. | ........... | 719/321 |
| 6,282,513 B1 * | 8/2001 | Strawder | ........... | 705/2 |
| 6,353,445 B1 * | 3/2002 | Babula et al. | ........... | 715/733 |
| 6,418,475 B1 * | 7/2002 | Fuchs | ........... | 709/238 |
| 6,424,996 B1 * | 7/2002 | Killcommons et al. | ........... | 709/206 |
| 6,509,914 B1 * | 1/2003 | Babula et al. | ........... | 715/762 |
| 6,564,256 B1 * | 5/2003 | Tanaka | ........... | 709/219 |
| 6,578,002 B1 * | 6/2003 | Derzay et al. | ........... | 705/2 |
| 6,598,011 B1 * | 7/2003 | Kucek et al. | ........... | 702/185 |
| 6,608,628 B1 * | 8/2003 | Ross et al. | ........... | 345/619 |
| 6,633,688 B1 * | 10/2003 | Nixon et al. | ........... | 382/305 |
| 6,656,120 B2 * | 12/2003 | Lee et al. | ........... | 600/437 |
| 6,691,134 B1 * | 2/2004 | Babula et al. | ........... | 707/104.1 |
| 6,697,783 B1 * | 2/2004 | Brinkman et al. | ........... | 705/3 |
| 6,807,543 B2 * | 10/2004 | Muthya | ........... | 707/10 |
| 6,901,371 B1 * | 5/2005 | Koritzinsky et al. | ........... | 705/2 |

(Continued)

*Primary Examiner*—Jeffrey Pwu
*Assistant Examiner*—Alicia Baturay
(74) *Attorney, Agent, or Firm*—Fletcher Yoder (57) ABSTRACT

A technique is provided for sharing clinical protocols for diagnostic imaging systems. The clinical protocols generally represent operational parameters, such as configuration data and procedures, which are clinically developed for a particular imaging diagnosis. An interface or access point, such as a network accessible database or website, is provided to facilitate the exchange of these clinical protocols between clinicians. The present technique also may facilitate the formation of new clinical protocols and/or the integration of new clinical protocols into various diagnostic imaging systems. Accordingly, clinicians can electronically exchange and configure a variety of imaging protocols for potentially greater quality in the particular imaging diagnosis.

48 Claims, 5 Drawing Sheets

U.S. PATENT DOCUMENTS

| | | | |
|---|---|---|---|
| 6,928,490 B1* | 8/2005 | Bucholz et al. | 709/249 |
| 6,931,270 B2* | 8/2005 | Daft et al. | 600/407 |
| 6,988,074 B2* | 1/2006 | Koritzinsky et al. | 705/2 |
| 7,016,952 B2* | 3/2006 | Mullen et al. | 709/224 |
| 7,020,651 B2* | 3/2006 | Ripley | 707/6 |
| 7,028,182 B1* | 4/2006 | Killcommons | 713/161 |
| 7,039,723 B2* | 5/2006 | Hu et al. | 709/248 |
| 7,054,823 B1* | 5/2006 | Briegs et al. | 705/2 |
| 7,383,196 B1* | 6/2008 | Tang et al. | 705/3 |
| 7,444,293 B1* | 10/2008 | Kahn et al. | 705/3 |
| 2001/0018659 A1* | 8/2001 | Koritzinsky et al. | 705/3 |
| 2002/0004798 A1* | 1/2002 | Babula et al. | 707/104.1 |
| 2002/0007284 A1* | 1/2002 | Schurenberg et al. | 705/2 |
| 2002/0016530 A1* | 2/2002 | Brown | 600/300 |
| 2002/0073429 A1* | 6/2002 | Beane et al. | 725/105 |
| 2002/0165735 A1* | 11/2002 | Stangel | 705/3 |
| 2002/0184325 A1* | 12/2002 | Killcommons et al. | 709/206 |
| 2003/0065669 A1* | 4/2003 | Kahn et al. | 707/100 |
| 2004/0024749 A1* | 2/2004 | Kusens | 707/3 |
| 2004/0249664 A1* | 12/2004 | Broverman et al. | 705/2 |
| 2005/0114181 A1* | 5/2005 | Gottlieb | 705/2 |
| 2005/0182657 A1* | 8/2005 | Abraham-Fuchs et al. | 705/2 |
| 2006/0064318 A1* | 3/2006 | Alsafadi et al. | 705/2 |
| 2006/0129326 A1* | 6/2006 | Braconnier et al. | 702/19 |
| 2006/0265253 A1* | 11/2006 | Rao et al. | 705/3 |

* cited by examiner

CLINICAL PROTOCOL QUERY

| INSTITUTION: | SELECT INSTITUTION ▽ | 192 |
| DATE SPAN: | SELECT DATE SPAN ▽ | 194 |
| FIELD STRENGTH: | SELECT FIELD STRENGTH ▽ | 196 |
| GRADIENT TYPE: | SELECT GRADIENT TYPE ▽ | 198 |
| REGION OF INTEREST (ROI): | SELECT ROI ▽ | 200 |

SUBMIT QUERY — 202

CLINICAL PROTOCOL DETAILS

PROTOCOL NAME:        PROTOCOL 218
SOFTWARE REVISION:    REVISION 220
FIELD STRENGTH:       FIELD STRENGTH 222
GRADIENT TYPE:        GRADIENT TYPE 224
REGION OF INTEREST (ROI): ROI 226
INSTITUTION:          INSTITUTION 228
DATE CREATED:         CREATION DATE 230

212 — IMAGE(S)    CLINICAL PROCEDURE AND ADVICE — 214

PROCEDURE — 216

232 — DOWNLOAD    234 — PRINT    SAVE — 236

METHOD AND SYSTEM FOR TRANSFER OF IMAGING PROTOCOLS AND PROCEDURES

BACKGROUND OF THE INVENTION

The present technique relates generally to diagnostic and imaging systems and, more particularly, to medical diagnostic imaging systems. Specifically, a technique is provided for electronically displaying, transferring, and sharing clinical protocols for a plurality of diagnostic imaging systems.

Diagnostic imaging systems, such as those in various medical modalities, generally use imaging protocols to define relevant parameters for acquiring and processing images. These imaging protocols are often transmitted by physical delivery of a computer disk, a printed document, or a hand-written document. Unfortunately, physical delivery (e.g., mail) can unacceptably delay a diagnostic procedure, which may be critical to a patient's diagnosis. Alternatively, a file transfer protocol (FTP) may be used to transfer the imaging protocol from one scanner to another. In either case, the imaging protocol is not necessarily workable with the desired diagnostic imaging system in its present form. The imaging protocol itself may have various errors, compatibility conflicts, and so forth. Moreover, the imaging protocol may not even represent validated operational parameters, such as uniform imaging criteria, uniform medical rules, and accepted clinical practices. Although manufacturers may provide standard protocols with its diagnostic imaging systems, these standard protocols are generally not validated or based on clinical expertise. The manufacturers simply do not have the expertise or regulatory permission to provide advice on specific clinical questions. In addition to these problems, the process of configuring the imaging protocol on the desired diagnostic imaging system often consumes considerable time and technical resources. For example, the manufacturer's representative and/or a resident clinician/technician may be needed to configure the diagnostic imaging system for the new imaging protocol.

Accordingly, a technique is needed to address one or more of the foregoing problems in the field of diagnostic imaging systems.

BRIEF DESCRIPTION OF THE INVENTION

A technique is provided for sharing clinical protocols for diagnostic imaging systems. The clinical protocols generally represent operational parameters, such as configuration data and procedures, which are clinically developed for a particular imaging diagnosis. An interface or access point, such as a network accessible database or website, is provided to facilitate the exchange of these clinical protocols between clinicians. The present technique also may facilitate the formation of new clinical protocols and/or the integration of new clinical protocols into various diagnostic imaging systems. Accordingly, clinicians can electronically exchange and configure a variety of imaging protocols for potentially greater quality in the particular imaging diagnosis.

BRIEF DESCRIPTION OF THE DRAWINGS

The foregoing and other advantages and features of the invention will become apparent upon reading the following detailed description and upon reference to the drawings in which.

DETAILED DESCRIPTION OF SPECIFIC EMBODIMENTS

Figure 1:
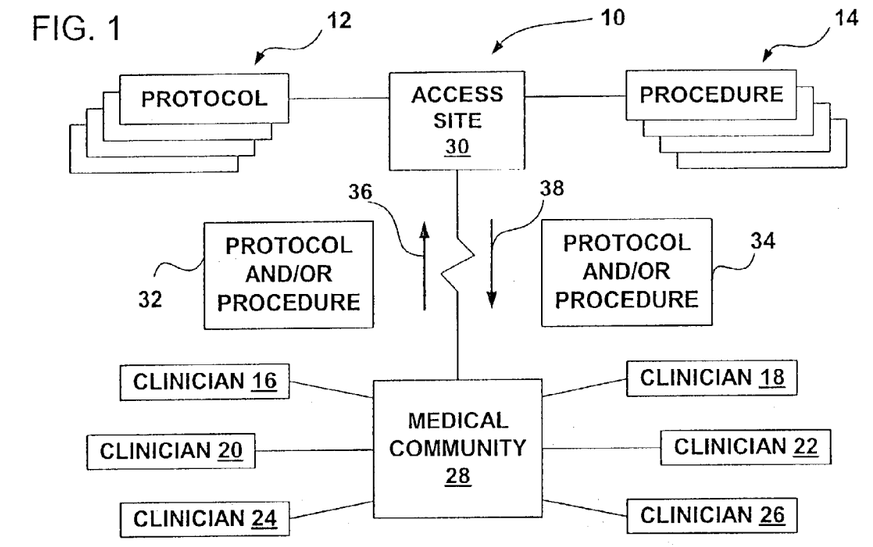
FIG. 1 is a diagram illustrating an exemplary protocol sharing system for exchanging clinical protocols and procedures between various clinicians in the medical community.

As discussed in detail below, the present technique facilitates the sharing of expertise in the field of diagnostic and imaging systems, such as medical diagnostic imaging systems. FIG. 1 is a diagram illustrating an exemplary protocol sharing system 10 for exchanging clinical protocols 12 and procedures 14 between various clinicians 16-26 in the medical community 28. As illustrated, the protocol sharing system 10 comprises a network database or site 30, which centralizes the exchange of the clinical protocols 12 and procedures 14. For example, any one of the clinicians 16-26 may develop and electronically transfer a new clinical protocol and/or procedure 32 (jointly or separately) to the network database or site 30, as indicated by arrow 36. The protocol sharing system 10 also may include a variety of approval or screening systems, such as clinical validity screening systems, to ensure the accuracy of clinical data stored in the network database or site 30. Once populated, the network database or site 30 may be queried for a particular clinical protocol and/or procedure. For example, any one of the clinicians 16-26 may request and acquire a desired clinical protocol and/or procedure 34 (jointly or separately) from the network database or site 30, as indicated by arrow 38. Accordingly, the protocol sharing system 10 functions as a peer-to-peer interface or melting-pot of clinical expertise in the area of diagnostic and imaging systems.

The foregoing clinical protocols 12 and procedures 14 may comprise a variety of clinically developed data. For example, the clinical protocols 12 may comprise various system identifiers, software versions and settings, hardware types and configurations, system orientations, acquisition parameters, processing parameters, analysis parameters, and other parameters clinically developed for the particular diagnosis. Moreover, the clinical protocols 12 may relate to a particular anatomy or region of interest, a particular focus (e.g., soft tissue versus bone structure), a particular pathology, a particular medical modality, and so forth. The clinical procedures 14 may correspond to technical know-how and clinical advice associated with the clinical protocols 12. However, the clinical procedures 14 also can include any practical information relating to diagnostic procedures, such as the acquisition, processing, and analysis of medical images.

Figure 2:
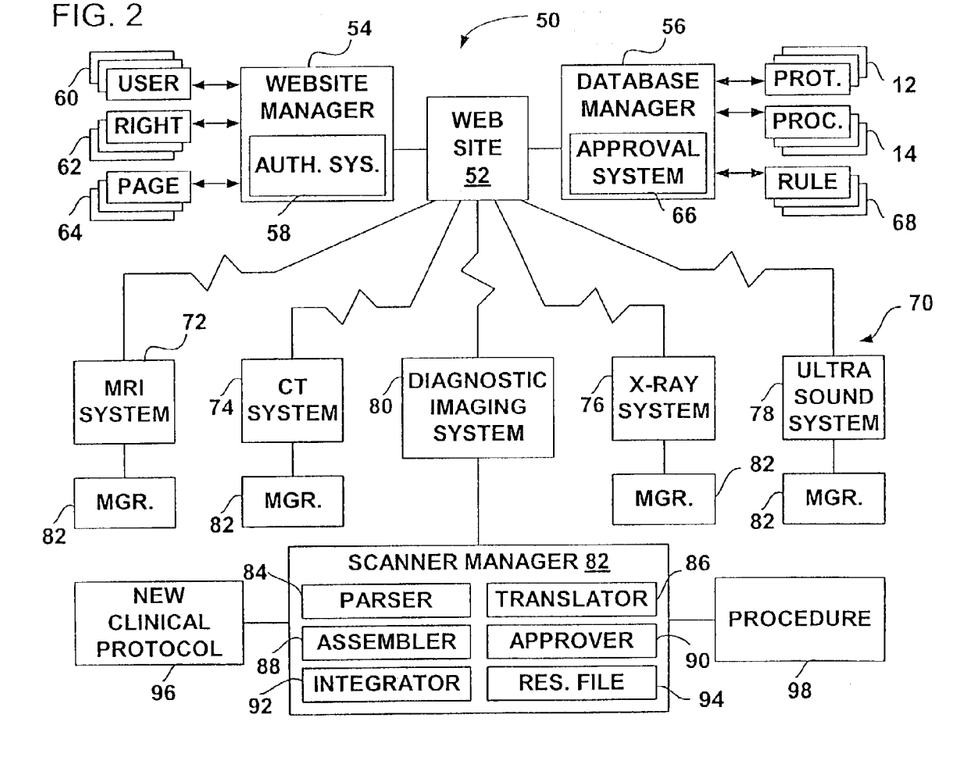
FIG. 2 is a diagram illustrating a Web-based system for exchanging clinical protocols and procedures with a plurality of medical imaging systems.

FIG. 2 is a diagram illustrating a Web-based system 50 for exchanging the clinical protocols 12 and procedures 14 in a plurality of medical imaging systems or modalities. As illustrated, the Web-based system 50 comprises a Website 52 having a Web manager 54 and a database manager 56. The Web manager 54 comprises a variety of control systems and software routines, which manage the content, appearance, and user access to the Website 52. For example, the illustrated Web manager 54 comprises a user authentication system 58, a plurality of authorized users 60, a plurality of user rights 62, and a plurality of Web-pages 64 available to the authorized users 60. It should be noted that the plurality of authorized users 60 may be limited to certain medical groups, hospitals, facilities, and clinicians within the medical community. However, a wide variety of authorized users 60 may be controlled by the user authentication system 58 based on the different user rights 62. For example, one of the authorized users 60 may have expertise in magnetic resonance imaging systems, while another one of the authorized users 60 may have expertise in ultrasound or x-ray systems. Accordingly, the rights 62 for these different users 60 may be tailored to their particular expertise or other criteria. To assign the appropriate user rights 62 to each authorized user 60, the user authentication system 58 also may request and evaluate a variety of user credentials to determine the appropriate user rights 62. For example, the user authentication system 58 may request academic credentials, clinical specialties and certifications, specific experience levels, proof of purchase or registration of a diagnostic or imaging system, and so forth. Accordingly, the various authorized users 60 may have rights 62 to the Webpages 64 ranging from restricted access to full unrestricted access.

As the Web manager 54 controls the content, appearance, and access to the Website 52, the database manager 56 controls the clinical protocols 12 and procedures 14. The database manager 56 comprises a variety of hardware and software routines, which generally control the access, retrieval, submission, modification, and exchange of clinical data at the Website 52. For example, the illustrated database manager 56 comprises an approval system 66 for the clinical protocols 12 and procedures 14. In operation, the approval system 66 analyzes each of the clinical protocols 12 and procedures 14 against a variety of eligibility criteria or screening rules 68, such as availability, readability, spelling, grammar, medical rules, legal and regulatory rules (e.g., FDA approval), and various other criteria affecting the quality and validity of the clinical protocols 12 and procedures 14. The database manager 56 also may perform a variety of clinical categorizing functions to organize the various clinical protocols 12 and procedures 14 into appropriate clinical groups. For example, the database manager 56 may comprise clinical categories based on a particular anatomy or region of interest, a particular focus (e.g., soft tissue versus bone structure), a particular pathology, a particular medical modality, a particular diagnostic system, a particular imaging system, particular hardware and software disposed on the system, and so forth.

As illustrated, the Web-based system 50 of FIG. 2 also provides Website 52 access to a plurality of diagnostic imaging systems 70, such as a magnetic resonance imaging (MRI) system 72, a computed tomography (CP) system 74, an x-ray system 76, an ultrasound system 78, and a diagnostic imaging system 80. At each of these diagnostic imaging systems 70, the Web-based system 50 provides a scanner manager 82 to facilitate the exchange of the clinical protocols 12 and procedures 14 with the medical community. In the illustrated embodiment, the scanner manager 82 coupled to the diagnostic imaging system 80 comprises a parser 84, a translator 86, an assembler 88, an approver 90, an integrator 92, and a resource file 94. The translator 86 uses the parser 84 to parse local protocols and extract desired protocol information based on criteria set in the resource file 94. For example, operational data may be acquired from configuration files, imaging protocols, hardware and software, scanner components, user input, and a variety of clinically developed parameters. The extracted information may relate to image acquisition, image processing, image analysis, and so forth. Moreover, the extracted information may be directed to certain anatomies, regions of interest, pathologies, and other specific medical areas. After acquiring the desired protocol information, the assembler 88 proceeds to gather, organize, and assemble the extracted information into a new clinical protocol 96. In addition, a clinician may create a new clinical procedure 98 having a variety of clinical advice, practical information, and expertise that may be useful for a particular diagnosis or imaging application. If desired, the new clinical procedure 98 can be combined with the new clinical protocol 96. It also should be noted that the foregoing data extraction, translation, and assembly process may be partially or entirely automated.

The clinical data disposed in the new clinical protocol 96 may be organized in a text file (e.g., an ASCII file), a database file, a spreadsheet file, a Web-file (e.g., HTML, XML, etc.), or any other suitable file type and format. For example, the new clinical protocol 96 may comprise a database file having a plurality of protocol items each having one or more entries. Possible protocol items may include a scan number, a coil name, an imaging plane/orientation, an imaging mode (e.g., 2D or 3D), a pulse sequence, a flip angle, a field of view, a slice thickness, a slice spacing, a number of slices, a matrix frequency, a matrix phase, a frequency direction, a center frequency, an auto shim status, a phase correction status, a scan time, imaging options, vascular options, gating options, and so forth. The new clinical protocol 96 also may comprise a variety of system information, such as field strength and gradient type of the imaging system, region of interest information, and hardware and software information (e.g., model number, serial number, software revision number, upgrades, modifications, etc.).

Once created, the new clinical protocol 96 and procedure 98 may be uploaded to the Website 52. For example, the user may interact with local software on the scanner manager 82 and/or an upload page on the Website 52. The upload process also may be subject to one or more approval mechanisms. In the illustrated embodiment of FIG. 2, the upload process is subject to approval by the approval system 66 upon receipt at the Website 52. For example, the scanner manager 82 may invoke one or both of the Web manager 54 and the database manager 56 to exchange the new clinical protocol 96 and procedure 98, to obtain approval of its data and format, to store the new clinical protocol 96 and procedure 98 at the database manager 56, and to post the new clinical protocol 96 and procedure 98 on one or more of the pages 64. However, the Web-based system 50 also may perform a variety of local validation routines using the approver 90. Similar to the approval system 66 at the Website 52, the scanner manager's approver 90 may analyze the new clinical protocol 96 and procedure 98 against a variety of eligibility criteria or screening rules, such as availability, readability, spelling, grammar, medical rules, legal and regulatory rules (e.g., FDA approval), and various other criteria affecting the quality and validity of the new clinical protocol 96 and procedure 98. If approved, then the new clinical protocol 96 and procedure 98 is stored at the database manager 56 for display on the Website 52. It also should be noted that the foregoing upload, approval, and Web-display process may be partially or entirely automated.

The scanner manager 82 of FIG. 2 also may facilitate the acquisition of a desired clinical protocol and/or procedure from the Website 52. If a user initiates a protocol and/or procedure download from the Website 52, then the scanner manager 82 may accept the download, save it to a specified directory, and initiate the approver 90 to evaluate the downloaded protocol and/or procedure. In operation, the approver 90 may analyze the downloaded protocol and/or procedure against a variety of eligibility criteria or screening rules, such as compatibility, source, version, and other factors affecting its workability with the diagnostic imaging system 80. If approved, then the downloaded protocol and/or procedure can be integrated into the diagnostic imaging system 80. For example, the scanner manager 82 may initiate the integrator 92, which performs various translation and configuration functions to setup the diagnostic imaging system 80 with the downloaded protocol and/or procedure. It also should be noted that the foregoing approval and integration functions of the scanner manager 82 may be partially or entirely automated.

Figure 3:
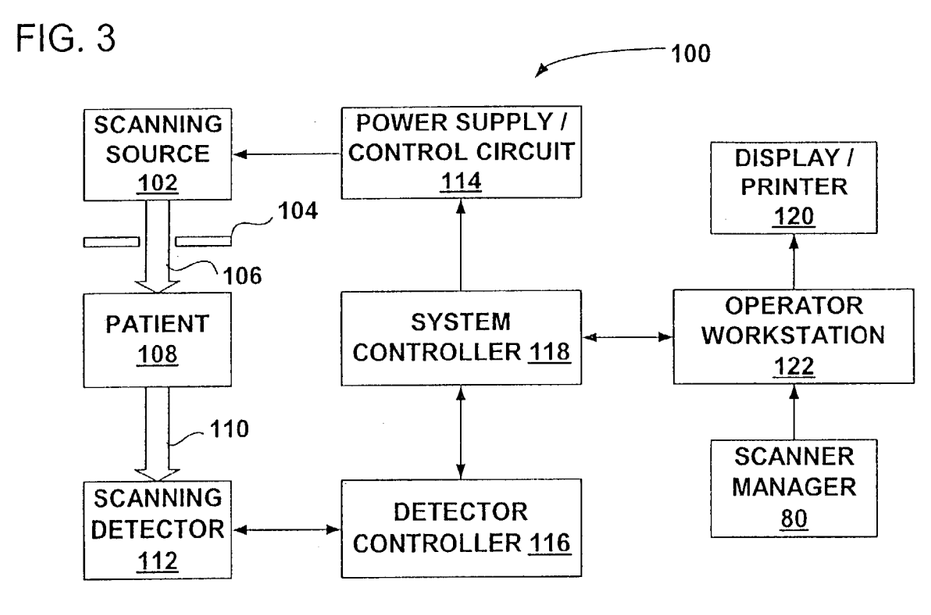
FIG. 3 is a diagram illustrating an exemplary diagnostic imaging system utilizing certain aspects of the systems illustrated in FIGS. 1 and 2.

FIG. 3 is a diagram illustrating an exemplary diagnostic imaging system 100 utilizing certain aspects of the systems 10 and 50 illustrated in FIGS. 1 and 2. In particular, the diagnostic imaging system 100 comprises the scanner manager 80 to facilitate the exchange of new clinical protocols and procedures with the Website 52. The illustrated diagnostic imaging system 100 represents a digital x-ray system, which includes a source of x-ray radiation 102 positioned adjacent to a collimator 104. Collimator 104 permits a stream 106 of radiation to pass into a region in which a subject, such as a human patient 108, is positioned. A portion of the radiation 110 passes through or around the subject and impacts a digital x-ray detector represented generally at reference numeral 112. As described more fully below, detector 112 converts the x-ray photons received on its surface to lower energy photons and, subsequently, to electrical signals that are acquired and processed to reconstruct an image of the features within the subject.

The scanning source 102 is controlled by a power supply/control circuit 114, which furnishes both power and control signals for examination sequences. Moreover, detector 112 is coupled to a detector controller 116 that commands acquisition of the signals generated in the detector. Detector controller 116 may also execute various signal processing and filtration functions, such as for adjustment of dynamic ranges, interleaving of digital image data, and so forth. Both power supply/control circuit 114 and detector controller 116 are responsive to signals from a system controller 118. In general, system controller 118 commands operation of the imaging system to execute examination protocols and to process acquired image data. Accordingly, system controller 118 will typically include a general purpose or application-specific computer, associated memory circuitry, interface circuits, and so forth. In the embodiment illustrated in FIG. 3, system controller 118 is linked to a display/printer 120 and to an operator workstation 122. In a typical system configuration, display/printer 120 will permit reconstructed images to be output for use by an attending physician or radiologist. Operator workstation 122 allows examinations to be commanded by a clinician or radiologist, permits system configurations to be reviewed, and so forth.

Figure 4:
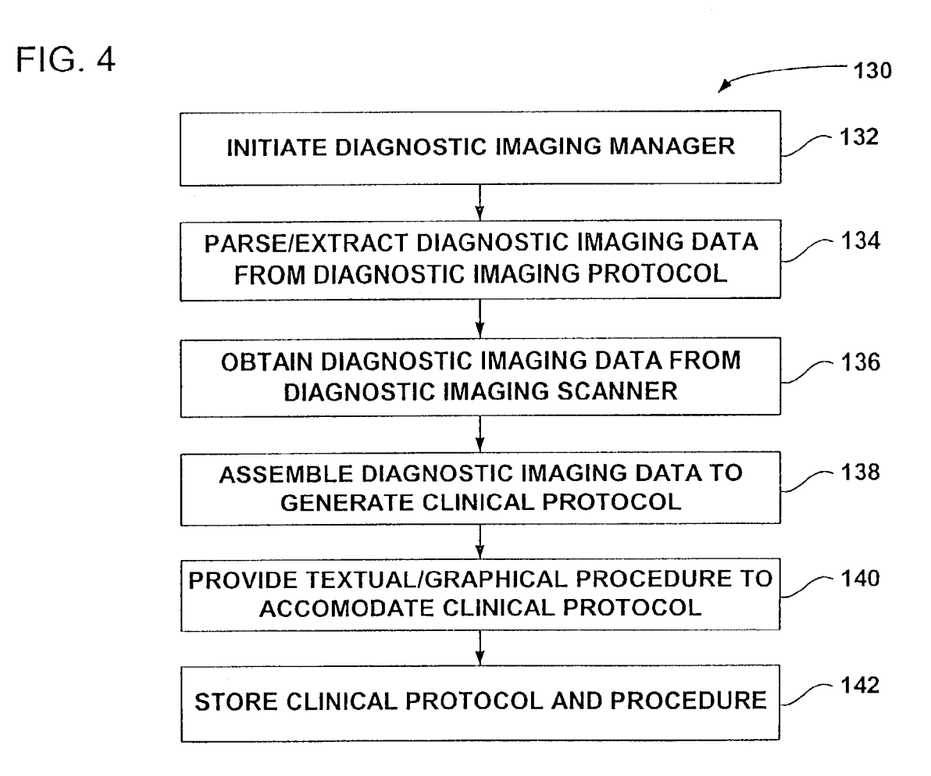
FIG. 4 is a flowchart illustrating an exemplary process for assembling a new clinical protocol.

FIG. 4 is a flowchart illustrating an exemplary process 130 for assembling a new clinical protocol. As illustrated in block 132, the process 130 proceeds by initiating a diagnostic imaging manager, such as the scanner manager 80. At block 134, the process 130 parses/extracts diagnostic imaging data from one or more diagnostic imaging protocols, such as operational parameters relating to the acquisition, processing, and analysis of medical images. For example, the protocol data may include various hardware and software settings developed to obtain a desired diagnostic image. The process 130 also obtains diagnostic imaging data from the diagnostic imaging scanner (block 136). For example, the scanner data may include hardware and software versions, model numbers, serial numbers, and various other identifying criteria. The process 130 then proceeds to assemble the diagnostic imaging data to generate a clinical protocol (block 138). At block 140, a textual/graphical procedure also may be formulated to accommodate the clinical protocol. For example, the clinician may provide practical advice relating to the diagnostic imaging scanner, the clinical protocol, and other related clinical/medical topics. As discussed above, the present technique may combine the clinical protocol and procedure into a single file. Alternatively, the clinical protocols and procedures may be maintained as separate clinical files. In either case, the process 130 then proceeds to store the clinical protocol and procedure (block 142).

Figure 5:
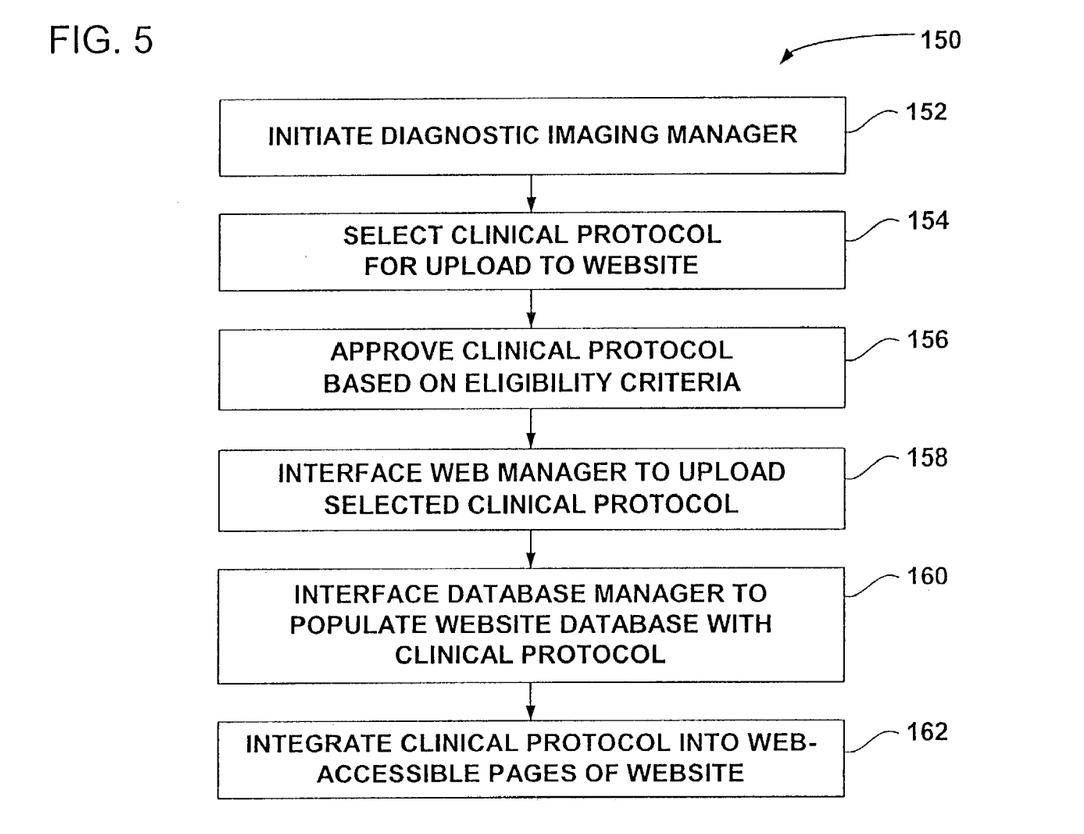
FIG. 5 is a flowchart illustrating an exemplary process for creating a network accessible database of clinical protocols.

FIG. 5 is a flowchart illustrating an exemplary process 150 for creating a network accessible database of clinical protocols, such as described with reference to FIGS. 1 and 2. As illustrated in block 152, the process 150 proceeds by initiating a diagnostic imaging manager, such as the scanner manager 80. At block 154, the process 150 selects a clinical protocol for upload to a Website. For example, the clinical protocol may correspond to the clinical protocol and/or clinical procedure developed according to FIGS. 1-4. Moreover, the Website may correspond to the network database or site 30 or the Website 52, as illustrated in FIGS. 1 and 2. The process 150 also may approve the clinical protocol based on a variety of eligibility criteria (block 156). For example, the process 150 may initiate the approval system 66 and/or the approver 90 illustrated in FIG. 2. The process 150 then proceeds to interface a Web manager to upload the selected clinical protocol to the Website (block 158). At block 160, the process 150 interfaces a database manager to populate the Website database with the selected clinical protocol (subject to prior approval). The clinical protocol is then integrated into Web-accessible pages of the Website (block 162). The foregoing process 150 also may be repeated to populate the website with a plurality of clinical protocols, which may relate to a wide variety of medical modalities and imaging systems.

Figure 6:
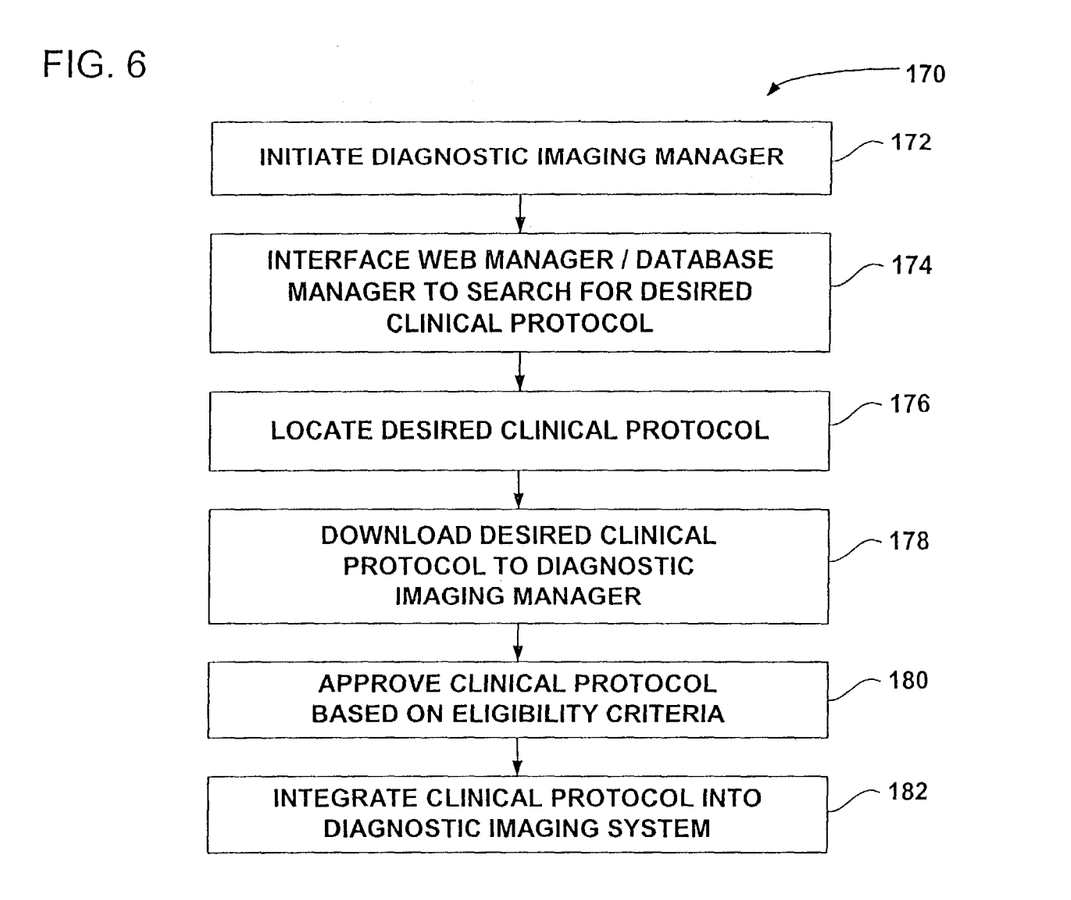
FIG. 6 is a flowchart illustrating an exemplary process for acquiring a desired clinical protocol for integration into a diagnostic imaging system.

FIG. 6 is a flowchart illustrating an exemplary process 170 for acquiring a desired clinical protocol for integration into a diagnostic imaging system. As illustrated in block 172, the process 170 proceeds by initiating a diagnostic imaging manager, such as the scanner manager 80. At block 174, the process 170 interfaces a Web manager and/or database manager to search for a desired clinical protocol. For example, the Web and database managers may correspond to the Web and database managers 54 and 56, as illustrated in FIG. 2. Moreover, the clinical protocol may correspond to the clinical protocol and/or procedure developed and uploaded according to FIGS. 1-5. Using the Web manager/database manager, the process 170 locates the desired clinical protocol at block 176. For example, the user may select a variety of clinical categories, system types, regions of interest, and other criteria to provide a list of one or more relevant clinical protocols. The process 170 then proceeds to download the desired clinical protocol to the diagnostic imaging manager (block 178). For example, the download process may occur automatically or after prompting the user to accept a download option. At block 180, the process 170 approves (or disapproves) the clinical protocol based on a variety of eligibility criteria. For example, the process 170 may evaluate the clinical protocol against compatibility criteria, source information, system information, and so forth. If the clinical protocol is approved at block 180, then the process 170 proceeds to integrate the clinical protocol into the diagnostic imaging system at block 182. For example, the process 170 may initiate the integrator 92 of FIG. 2. Otherwise, the process 170 rejects the clinical protocol and does not use it for the diagnostic imaging system.

Figure 7:
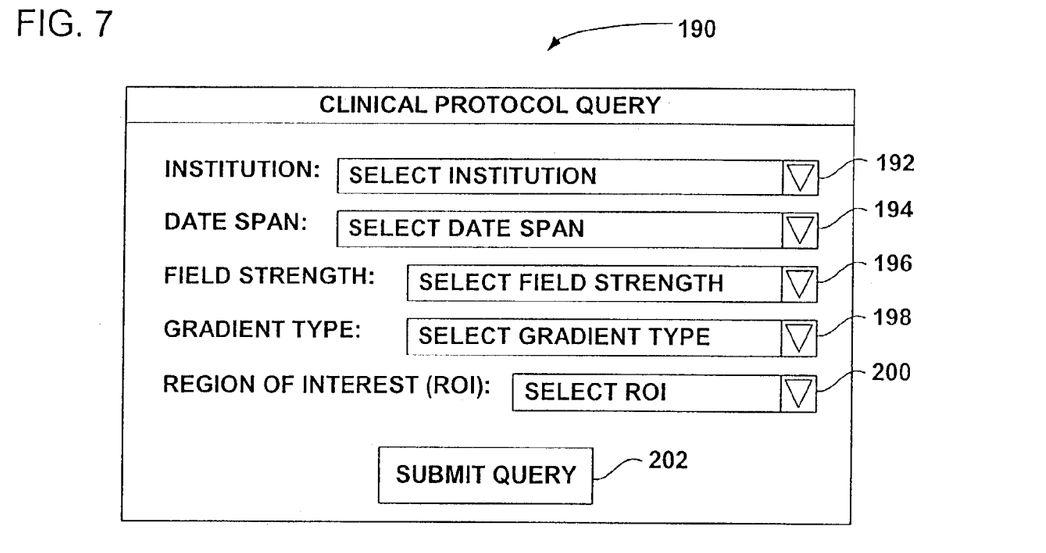
FIGS. 7 and 8 are diagrams illustrating exemplary user interfaces for acquiring the desired clinical protocol.
Figure 8:
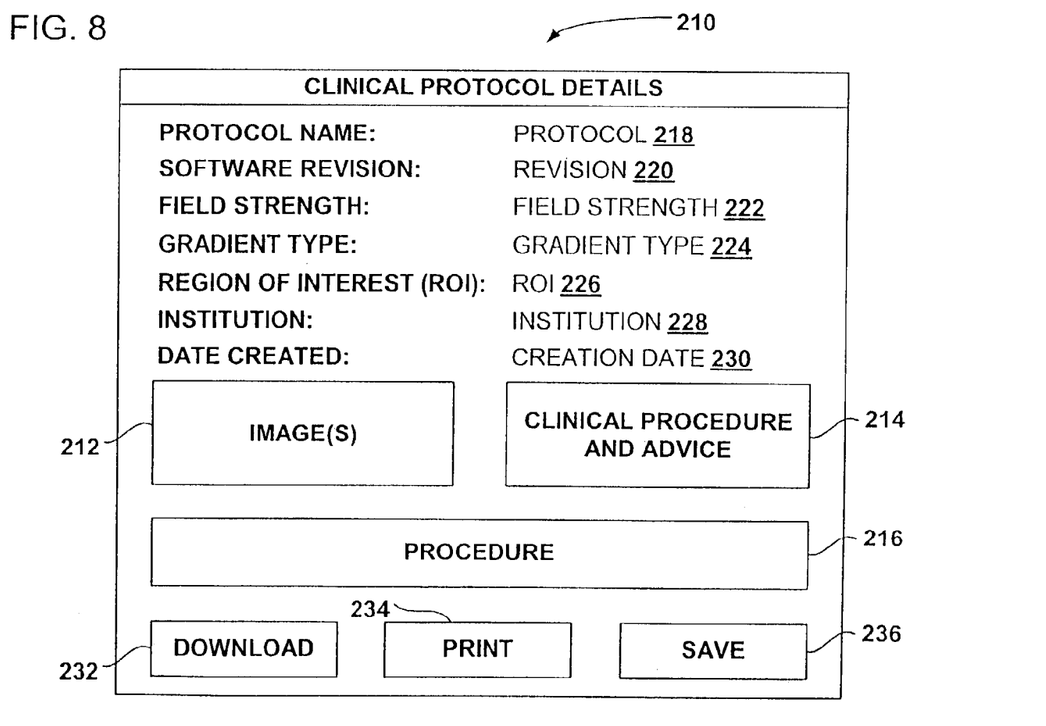

FIGS. 7 and 8 are diagrams illustrating exemplary user interfaces for acquiring the desired clinical protocol. For example, FIG. 7 illustrates a Clinical Protocol Query page 190 for acquiring a desired clinical protocol from the network accessible database or site, such as the Website 52 illustrated in FIG. 2. As illustrated, the clinical protocol query page 190 comprises a Select Institution drop-down menu 192, a Select Date Span drop-down menu 194, a Select Field Strength drop-down menu 196, a Select Gradient Type drop-down menu 198, and a Select Region Of Interest (ROI) drop-down menu 200. The Select Institution drop-down menu 192 may comprise a variety of hospitals and other service facilities, medical schools, medical research institutions, and other sources. The Select Field Strength and Select Gradient Type drop-down menus 196 and 198 also may comprise a wide variety of categories, which narrow the search to a smaller range of diagnostic and imaging systems. The Select Region Of Interest (ROI) drop-down menu 200 can include a list of anatomies, soft tissues, bone structure, pathologies, and so forth. After selecting categories from one or more of the drop-down menus 192-200, the user may click a Submit Query button 202 to execute the search for the desired clinical protocol. Although specific drop-down menus are provided in the clinical protocol query page 190, the present technique may use a wide variety of other categories and keyword searches to facilitate the search process.

Turning now to FIG. 8, the present technique may display the details of the Desired Clinical Protocol in a page 210. For example, the Clinical Protocol Details page 210 may represent a web-page acquired and displayed by the Website 52 of FIG. 2. As illustrated, the page 210 displays one or more images 212, clinical procedures and advice 214, and clinical protocols and imaging information 216. For example, the one or more images 212 may correspond to actual diagnostic images obtained using the clinical protocol and imaging information 216. This graphical information allows the user to quickly evaluate the usefulness and scope of the clinical protocol and imaging information 216. The page 210 also may provide a variety of other data, such as a protocol name 218, a software revision identifier 220, a field strength 222, a gradient type 224, a specific region of interest 226, a specific source or institution 228, and a creation date 230. The user can also download, print, or save the clinical protocol (and corresponding data) by clicking on a download button 232, a print button 234, or a save button 236, respectively. Various other user interaction pages are also within the scope of the present technique.

While the invention may be susceptible to various modifications and alternative forms, specific embodiments have been shown by way of example in the drawings and have been described in detail herein. However, it should be understood that the invention is not intended to be limited to the particular forms disclosed. Rather, the invention is to cover all modifications, equivalents, and alternatives falling within the spirit and scope of the invention as defined by the following appended claims.

What is claimed is:

1. A method of sharing protocols for diagnostic imaging systems, comprising:

receiving a clinical protocol from a first diagnostic imaging system via a network interface, the clinical protocol including operational protocols and procedures clinically developed for the first diagnostic imaging system, wherein the act of receiving the clinical protocol comprises the act of verifying rights of a user to upload the clinical protocol, and wherein the act of verifying rights of the user comprises the act of authenticating the user as a medical clinician;

validating the clinical protocol based on screening parameters, wherein the validating includes analyzing the clinical protocol against eligibility criteria to ensure quality and to approve the protocol for integration into a network accessible database comprising a plurality of different clinical protocols, and wherein the eligibility criteria comprise diagnostic imaging system compatibility criteria, source information indicative of authorized users, and software version information;

storing the clinical protocol on the network accessible database;

displaying the clinical protocol to an inquiring user of a plurality of clinical users; and providing a download option for the inquiring user to obtain the clinical protocol for a second diagnostic imaging system;

wherein the act of receiving, storing, displaying, and providing comprises the act of facilitating clinician-to-clinician development of operational parameters and procedures for the diagnostic imaging systems.

2. The method of claim 1, wherein the act of receiving the clinical protocol comprises the act of authenticating the clinical protocol based on a set of clinical rules.

3. The method of claim 1, wherein the act of displaying the clinical protocol comprises the act of populating a web-page with data representative of the clinical protocol.

4. The method of claim 1, wherein the act of displaying the clinical protocol comprises the act of sharing clinical advice correlating to the clinical protocol.

5. A method of sharing protocols for diagnostic imaging systems, comprising:

extracting clinical protocols from a plurality of diagnostic imaging systems via a network interface;

assembling a network accessible database comprising clinical protocols for the plurality of diagnostic imaging systems, wherein the act of assembling a network accessible database comprises the act of verifying rights of a user to upload the clinical protocol, and wherein the act of verifying rights of the user comprises the act of authenticating the user as a medical clinician;

displaying options for uploading and downloading the clinical protocols via the network interface; and controlling data representative of the clinical protocols based on a set of rules that includes validating the clinical protocols against a plurality of uniform medical parameters, wherein the validating includes analyzing the clinical protocol against eligibility criteria to ensure workability with at least one of the plurality of diagnostic imaging systems and to approve the protocol for integration into the at least one diagnostic imaging system, and wherein the eligibility criteria comprise diagnostic imaging system compatibility criteria, source information indicative of authorized users, and software version information;

wherein the act of extracting, assembling, displaying options, and controlling data comprises the act of facilitating clinician-to-clinician development of operational parameters and procedures for the plurality of diagnostic imaging systems.

6. The method of claim 5, wherein the clinical protocols are developed by clinicians having diagnostic imaging expertise.

7. The method of claim 5, wherein the act of extracting the clinical protocols comprises the act of automatically creating the clinical protocols based at least partially on clinical data.

8. The method of claim 5, wherein the act of displaying options for uploading and downloading the clinical protocols comprises the act of populating web-pages with data representative of the clinical protocols.

9. The method of claim 5, wherein the act of controlling data representative of the clinical protocols comprises the act of verifying the diagnostic imaging expertise of each of the clinicians.

10. The method of claim 5, wherein the act of controlling data representative of the clinical protocols comprises the act of verifying rights of a user to exchange clinical data with the network accessible database.

11. The method of claim 5, wherein the acts of assembling, displaying, and controlling comprise the act of facilitating improved operation of the diagnostic imaging systems based on clinician-to-clinician expertise sharing.

12. A method of sharing protocols for diagnostic imaging systems, comprising:
    extracting diagnostic imaging data from a first diagnostic imaging system;
    parsing operational parameters correlating to a desired image diagnostic, the image diagnostic being part of the extracted data;
    creating a uniform clinical protocol based at least partially on the operational parameters;
    electronically transferring the uniform clinical protocol to a network accessible database comprising a plurality of clinically developed protocols for diagnostic imaging systems, wherein the act of electronically transferring the clinical protocol comprises the act of verifying rights of a user to upload the clinical protocol, and wherein the act of verifying rights of the user comprises the act of authenticating the user as a medical clinician; and
    validating the uniform clinical protocol against a set of validation parameters, wherein the validating includes analyzing the clinical protocol against eligibility criteria to ensure quality and to approve the protocol for storage in the network accessible database, and wherein the eligibility criteria comprise diagnostic imaging system compatibility criteria, source information indicative of authorized users, and software version information;
    wherein the act of extracting, parsing, creating, and electronically transferring comprises the act of facilitating clinician-to-clinician development of operational parameters and procedures for the diagnostic imaging systems.

13. The method of claim 12, wherein the act of parsing operational parameters comprises the act of obtaining identification data representative of the first diagnostic imaging system and imaging settings clinically developed for the desired image diagnostic.

14. The method of claim 12, wherein the act of creating the uniform clinical protocol comprises the act of assembling image acquisition and processing settings clinically developed for the first diagnostic imaging system.

15. The method of claim 12, wherein the act of creating the uniform clinical protocol further comprises the act of providing clinically developed procedures corresponding to the uniform clinical protocol.

16. The method of claim 12, wherein the act of electronically transferring comprises the act of uploading the uniform clinical protocol via a Web interface communicative with the network accessible database.

17. The method of claim 12, wherein the act of electronically transferring comprises the act of categorizing the uniform clinical protocol by a diagnostic region of interest.

18. The method of claim 12, wherein the act of electronically transferring comprises the act of categorizing the uniform clinical protocol into one of a plurality of medical modalities.

19. The method of claim 12, wherein the act of electronically transferring comprises the act of categorizing the uniform clinical protocol by a field strength and gradient type of diagnostic imaging scanner.

20. The method of claim 12, comprising the act of displaying the uniform clinical protocol to at least one of a plurality of clinicians via a network interface communicative with the network accessible database.

21. The method of claim 12, comprising the act of transferring the uniform clinical protocol to a requesting clinician.

22. The method of claim 12, comprising the act of routing the uniform clinical protocol to a second diagnostic imaging system remote from the first diagnostic imaging system.

23. The method of claim 22, wherein the act of routing the uniform clinical protocol comprises the act of automatically configuring the second diagnostic imaging system with the uniform clinical protocol.

24. A method of sharing protocols for diagnostic imaging systems, comprising:
    searching a network accessible database comprising a plurality of clinically-based protocols for diagnostic imaging systems, the clinically-based protocols including operational protocols and procedures clinically developed from a diagnostic imaging system;
    locating a desired protocol of the plurality of clinically-based protocols; and
    downloading the desired protocol to another diagnostic imaging system, wherein the act of downloading the desired protocol comprises the act of verifying rights of a user to download the clinical protocol, and wherein the act of verifying rights of the user comprises the act of authenticating the user as a medical clinician; and
    validating operability of the desired protocol with the another diagnostic imaging system, wherein the validating includes analyzing the clinical protocol against eligibility criteria to ensure quality and to approve the protocol for integration into the diagnostic imaging system, and wherein the eligibility criteria comprise diagnostic imaging system compatibility criteria, source information indicative of authorized users, and software version information;
    wherein the act of searching, locating, and downloading comprises the act of facilitating clinician-to-clinician development of operational parameters and procedures for the diagnostic imaging systems.

25. The method of claim 24, wherein the act of searching a network accessible database comprises the act of interfacing the network accessible database via a Web interface.

26. The method of claim 24, wherein the act of searching the network accessible database comprises the act of browsing pages that are hierarchically organized based on clinical categories.

27. The method of claim 24, wherein the act of searching the network accessible database comprises the act of relaying a search query to the network accessible database to extract a desired portion of the plurality of clinically-based protocols.

28. The method of claim 24, wherein the act of searching the network accessible database comprises the act of selecting at least one of a plurality of medical modalities.

29. The method of claim 24, wherein the act of searching the network accessible database comprises the act of selecting a diagnostic region of interest.

30. The method of claim 24, wherein the act of searching the network accessible database comprises the act of selecting a field strength and gradient type of a medical imaging scanner.

31. The method of claim 24, wherein the act of locating the desired protocol comprises the act of acquiring clinical data developed from a plurality of different clinical sources.

32. The method of claim 24, comprising the act of automatically integrating the desired protocol into the diagnostic imaging system.

33. The method of claim 24, comprising the act of executing clinical procedures accompanying the desired protocol.

34. The method of claim 24, comprising acquiring a medical diagnostic image with the diagnostic imaging system based on the desired protocol.

35. A system of sharing protocols for diagnostic imaging systems, comprising:
   a network accessible database of clinical protocols for a plurality of diagnostic imaging systems, the clinical protocols including operational protocols and procedures clinically developed from a diagnostic imaging system;
   an interface comprising upload and download options for the clinical protocols; and
   a clinical-rules-based controller comprising a plurality of authorized users identifying medical clinicians and comprising protocol transfer rules, the controller configured to verify rights of a user to upload the clinical protocol by authenticating the user as one of the plurality of authorized users, the controller configured to validate the clinical protocols by analyzing the clinical protocols against eligibility criteria including a plurality of uniform medical parameters to ensure quality and to approve each of the clinical protocols for integration into an additional diagnostic imaging system, and wherein the eligibility criteria comprise diagnostic imaging system compatibility criteria, source information indicative of authorized users, and software version information;
   wherein the interface and the clinical-rules-based controller are configured to facilitate clinician-to-clinician development of operational parameters and procedures for the plurality of diagnostic imaging systems.

36. The system of claim 35, wherein the clinical protocols are representative of a plurality of medical modalities.

37. The system of claim 35, wherein the clinical protocols are representative of a plurality of clinicians and medical expertise.

38. The system of claim 35, wherein the interface comprises a Web interface communicative with the network accessible database.

39. The system of claim 35, wherein the interface comprises a query page having a plurality of image diagnostic criteria that categorize the clinical protocols.

40. The system of claim 39, wherein the plurality of image diagnostic criteria comprise a plurality of diagnostic regions of interest.

41. The system of claim 39, wherein the plurality of image diagnostic criteria comprise a plurality of gradient types and field strengths for different image diagnostic scanners.

42. The system of claim 35, wherein the clinical-rules-based controller comprises a clinical expertise verification system for the plurality of authorized users.

43. The system of claim 35, wherein the clinical-rules-based controller comprises a protocol approval system having a plurality of screening parameters for the clinical protocols.

44. The system of claim 35, comprising an operational data extractor adapted to extract clinically-developed operational data from a desired diagnostic imaging system.

45. The system of claim 44, wherein the operational data extractor comprises a resource file specifying desired extraction data.

46. The system of claim 44, comprising a protocol assembler adapted to assemble a clinical protocol based at least partially on the clinically- and developed operational data.

47. A medical diagnostic imaging system, comprising:
   a scanner;
   a scanner controller having operational parameters developed by clinical expertise;
   means for extracting clinical data from the operational parameters;
   means for assembling a clinical protocol based at least partially on the clinical data;
   means for sharing the clinical protocol with a networked community of clinicians by verifying rights of a user to upload the clinical protocol by authenticating the user as a medical clinician; and
   means for validating and approving the clinical protocol by analyzing the clinical protocol against eligibility criteria including a plurality of uniform medical parameters to ensure quality and to approve the protocol for integration into the diagnostic imaging system, wherein the eligibility criteria comprise diagnostic imaging system compatibility criteria, source information indicative of authorized users, and software version information;
   wherein the means for assembling the clinical protocol and the means for sharing the clinical protocol are capable of facilitating clinician-to-clinician development of operational parameters and procedures for the plurality of diagnostic imaging systems.

48. A computer program product comprising:
   at least one machine readable medium;
   computer code stored on the at least one machine readable medium comprising instructions for extracting clinically-developed operational parameters from a desired diagnostic imaging system, creating a clinical protocol based at least partially on the extracted clinically-developed operational parameters, electronically transferring the clinical protocol to a network accessible database of clinical protocols developed by clinicians for diagnostic imaging systems and validating the clinical protocol, and facilitating clinician-to-clinician development of operational parameters and procedures for the diagnostic imaging systems, wherein the electronically transferring includes verifying rights of a user to upload the clinical protocol by authenticating the user as a medical clinician wherein the validating includes analyzing the clinical protocol against a set of screening rules to ensure quality and to approve the clinical protocol for integration into the network accessible database, and wherein the screening rules comprise diagnostic imaging system compatibility criteria, source information indicative of authorized users, and software version information.

* * * * *